United States Patent [19]
Coates et al.

[11] Patent Number: 5,989,289
[45] Date of Patent: Nov. 23, 1999

[54] BONE GRAFTS

[75] Inventors: Bradley J. Coates, Rossville; James Van Hoeck, Cordova; Jeffrey Poyner, Atoka, all of Tenn.

[73] Assignee: SDGI Holdings, Inc., Wilmington, Del.

[ * ] Notice: This patent is subject to a terminal disclaimer.

[21] Appl. No.: 08/948,135

[22] Filed: Oct. 9, 1997

Related U.S. Application Data

[63] Continuation of application No. 08/902,937, Jul. 30, 1997, abandoned, which is a continuation-in-part of application No. 08/740,031, Oct. 23, 1996, which is a continuation-in-part of application No. 08/603,676, Feb. 20, 1996, abandoned, which is a continuation-in-part of application No. 08/543,563, Oct. 16, 1995, abandoned, and a continuation-in-part of application No. 08/603,675, Feb. 20, 1996, abandoned, which is a continuation-in-part of application No. 08/543,563, Oct. 16, 1995, abandoned.

[51] Int. Cl.⁶ ........................................................ A61F 2/44
[52] U.S. Cl. ................................................................ 623/17
[58] Field of Search ................................ 623/17, 18, 21; 606/61

[56] References Cited

U.S. PATENT DOCUMENTS 4,685,919  8/1987  Niwa et al. ................................ 623/21

FOREIGN PATENT DOCUMENTS 2703580  10/1994  France ...................................... 623/17

Primary Examiner—David J. Isabella
Attorney, Agent, or Firm—Woodard, Emhardt, Naughton, Moriarty & McNett

[57] ABSTRACT

A spinal spacer 300 for engagement between vertebrae is provided which includes a body 301 formed of a bone composition. The body 301 includes a first end 311, an opposite second 315 end, a superior face 335 defining a superior vertebral engaging surface 337 and an inferior face 338 defining an inferior vertebral engaging surface 340. At least one of the vertebral engaging surfaces defines a set of migration resistance grooves 350. Each of the grooves 350 includes a first face 355 defining an angle of no more than about 90 degrees relative to the engaging surface 340 and a second opposing sloped face 360. The first and second faces 355, 360 define an arcuate pocket 370 therebetween for trapping vertebral bone to resist migration of the spacer 300. In one embodiment, the grooves 350 are arranged in series in that all of the second faces 360 slope in the same direction.

24 Claims, 11 Drawing Sheets

BONE GRAFTS

This application is a continuation of Ser. No. 08/902,937, filed Jul. 30, 1997, now abandoned, which is a continuation-in-part application of Ser. No. 08/740,031, filed Oct. 23, 1996, pending, which is a continuation-in-part application of Ser. No. 08/603,676 filed Feb. 20, 1996, now abandoned, which is a continuation-in-part application of Ser. No. 08/543,563 filed Oct. 16, 1995, now abandoned; and Ser. No. 08/603,675, filed Feb. 20, 1996, now abandoned, which is a continuation-in-part application of Ser. No. 08/543,563 filed Oct. 16, 1995, now abandoned.

FIELD OF THE INVENTION

The present invention relates to spacers, compositions, instruments and methods for arthrodesis. In specific applications of the invention the spacers include bone grafts having advantageous shapes and surface features.

BACKGROUND OF THE INVENTION

Spinal fusion is indicated to provide stabilization of the spinal column for painful spinal motion and disorders such as structural deformity, traumatic instability, degenerative instability, and post-resection iatrogenic instability. Fusion, or arthrodesis, is achieved by the formation of an osseous bridge between adjacent motion segments. This can be accomplished within the disc space, anteriorly between contiguous vertebral bodies or posteriorly between consecutive transverse processes, laminae or other posterior aspects of the vertebrae.

An osseous bridge, or fusion mass, is biologically produced by the body upon skeletal injury. This normal bone healing response is used by surgeons to induce fusion across abnormal spinal segments by recreating spinal injury conditions along the fusion site and then allowing the bone to heal. A successful fusion requires the presence of osteogenic or osteopotential cells, adequate blood supply, sufficient inflammatory response, and appropriate preparation of local bone. This biological environment is typically provided in a surgical setting by decortication, or removal of the outer, cortical bone to expose the vascular, cancellous bone, and the deposition of an adequate quantity of high quality graft material.

A fusion or arthrodesis procedure is often performed to treat an anomaly involving an intervertebral disc. Intervertebral discs, located between the endplates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosis. In a healthy, undamaged spine, the annulus fibrosis prevents the nucleus pulposus from protruding outside the disc space.

Spinal discs may be displaced or damaged due to trauma, disease or aging. Disruption of the annulus fibrosis allows the nucleus pulposus to protrude into the vertebral canal, a condition commonly referred to as a herniated or ruptured disc. The extruded nucleus pulposus may press on the spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

Sometimes the only relief from the symptoms of these conditions is a discectomy, or surgical removal of a portion or all of an intervertebral disc followed by fusion of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain. Pain relief via discectomy and arthrodesis requires preservation of the disc space and eventual fusion of the affected motion segments.

Bone grafts are often used to fill the intervertebral space to prevent disc space collapse and promote fusion of the adjacent vertebrae across the disc space. In early techniques, bone material was simply disposed between the adjacent vertebrae, typically at the posterior aspect of the vertebrae, and the spinal column was stabilized by way of a plate or rod spanning the affected vertebrae. Once fusion occurred the hardware used to maintain the stability of the segment became superfluous and was a permanent foreign body. Moreover, the surgical procedures necessary to implant a rod or plate to stabilize the level during fusion were frequently lengthy and involved.

It was therefore determined that a more optimal solution to the stabilization of an excised disc space is to fuse the vertebrae between their respective end plates, preferably without the need for anterior or posterior plating. There have been an extensive number of attempts to develop an acceptable intra-discal implant that could be used to replace a damaged disc and maintain the stability of the disc interspace between the adjacent vertebrae, at least until complete arthrodesis is achieved. To be successful the implant must provide temporary support and allow bone ingrowth. Success of the discectomy and fusion procedure requires the development of a contiguous growth of bone to create a solid mass because the implant may not withstand the cyclic compressive spinal loads for the life of the patient.

Many attempts to restore the intervertebral disc space after removal of the disc have relied on metal devices. U.S. Pat. No. 4,878,915 to Brantigan teaches a solid metal plug. U.S. Pat. Nos. 5,044,104; 5,026,373 and 4,961,740 to Ray; 5,015,247 to Michelson and U.S. Pat. No. 4,820,305 to Harms et al., U.S. Pat. Nos. 5,147,402 to Bohler et al. and 5,192,327 to Brantigan teach hollow metal cage structures. Unfortunately, due to the stiffness of the material, some metal implants may stress shield the bone graft, increasing the time required for fusion or causing the bone graft to resorb inside the cage. Subsidence, or sinking of the device into bone, may also occur when metal implants are implanted between vertebrae if fusion is delayed. Metal devices are also foreign bodies which can never be fully incorporated into the fusion mass.

Various bone grafts and bone graft substitutes have also been used to promote osteogenesis and to avoid the disadvantages of metal implants. Both allograft and autograft are biological materials which are replaced over time with the patient's own bone, via the process of creeping substitution. Over time a bone graft virtually disappears unlike a metal implant which persists long after its useful life. Stress shielding is avoided because bone grafts have a similar modulus of elasticity as the surrounding bone. Commonly used implant materials have stiffness values far in excess of both cortical and cancellous bone. Titanium alloy has a stiffness value of 114 Gpa and 316L stainless steel has a stiffness of 193 Gpa. Cortical bone, on the other hand, has a stiffness value of about 17 Gpa. Moreover, bone as an implant also allows excellent postoperative imaging because it does not cause scattering like metallic implants on CT or MRI imaging.

Various spacers have been constructed from bone or graft substitute materials to fill the intervertebral space after the removal of the disc. For example, the Cloward dowel is a circular graft made by drilling an allogenic or autogenic plug from the illium. Cloward dowels are bicortical, having porous cancellous bone between two cortical surfaces. Such dowels have relatively poor biomechanical properties, in particular a low compressive strength. Therefore, the Cloward dowel is not suitable as an intervertebral spacer without internal fixation due to the risk of collapsing prior to fusion under the intense cyclic loads of the spine.

Unfortunately, the use of bone grafts presents several disadvantages. Autograft is available in only limited quantities. The additional surgery also increases the risk of infection and blood loss and may reduce structural integrity at the donor site. Furthermore, some patients complain that the graft harvesting surgery causes more short-term and long-term pain than the fusion surgery.

Both allograft and autograft present additional difficulties. Graft alone may not provide the stability required to withstand spinal loads. Internal fixation can address this problem but presents its own disadvantages such as the need for more complex surgery as well as the disadvantages of metal fixation devices. Also, the surgeon is often required to repeatedly trim the graft material to obtain the correct size to fill and stabilize the disc space. This trial and error approach increases the length of time required for surgery. Furthermore, the graft material usually has a smooth surface which does not provide a good friction fit between the adjacent vertebrae. Migration and expulsion of the graft may cause neural and vascular injury, as well as collapse of the disc space. Even where such slippage does not occur, micromotion at the graft/fusion-site interface may disrupt the healing process that is required for fusion.

Several attempts have been made to develop a bone graft substitute which avoids the disadvantages of metal implants and bone grafts while capturing advantages of both. In each case, developing an implant having the biomechanical properties of metal and the biological properties of bone without the disadvantages of either has been extremely difficult or impossible.

A need has remained for fusion spacers which stimulate bone ingrowth and provide sufficient strength to support the vertebral column until the adjacent vertebrae are fused yet avoid the disadvantages of graft migration, stress shielding and the presence of a permanent foreign body.

SUMMARY OF THE INVENTION

In accordance with one aspect of the invention, spinal spacers and compositions are provided for fusion of a motion segment. Spacers include a load bearing body sized for engagement within the space between adjacent vertebrae after discectomy to maintain the space. The body is formed of a bone composition and includes a first end defining a first surface, an opposite second end defining a second surface, a superior face defining a superior vertebral engaging surface and an inferior face defining an inferior vertebral engaging surface. The spacers include means for resisting migration. In one embodiment, the means include a set of migration resistant grooves defined in at least one of the vertebral engaging surfaces. Each of the grooves includes a first face defining an angle of no more than about 90° relative to the engaging surface and a second opposing sloped face. The first and second faces define a pocket therebetween for trapping vertebral bone. In another embodiment the set of grooves is defined in the first portion of the engaging surface and a second set of migration resistant grooves is defined in a second portion of the surface to resist migration in two directions.

One object of the invention is to provide spacers for engagement between vertebrae which resist migration of the implanted spacers, yet encourage bone ingrowth and avoid stress shielding. Another object of the invention is to provide a spacer which restores the intervertebral disc space and supports the vertebral column while promoting bone ingrowth.

One benefit of the spacers of the present invention is that they combine the advantages of bone grafts with the advantages of metals, without the corresponding disadvantages. An additional benefit is that the invention provides a stable scaffold for bone ingrowth before fusion occurs. Still another benefit of this invention is that it allows the use of bone grafts without the need for metal cages or internal fixation, due to the compressive strength of the spacer and the means for resisting migration. Other objects and further benefits of the present invention will become apparent to persons of ordinary skill in the art from the following written description and accompanying Figures.

DESCRIPTION OF THE PREFERRED EMBODIMENT

Figure 1:
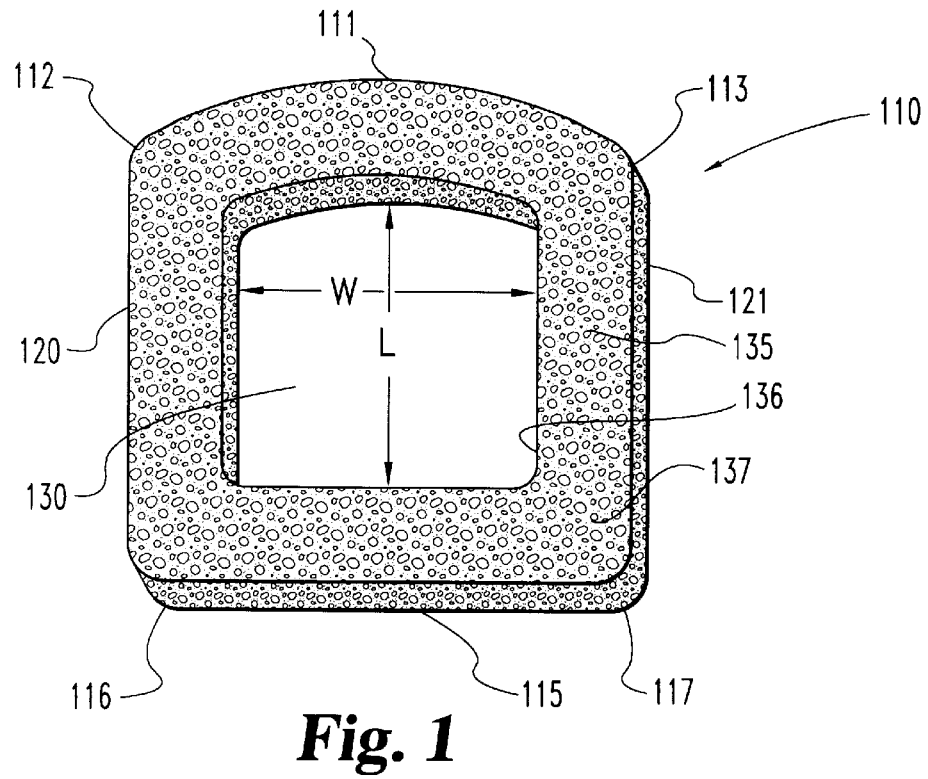
FIG. 1 is a D-shaped spacer of this invention.
Figure 2:
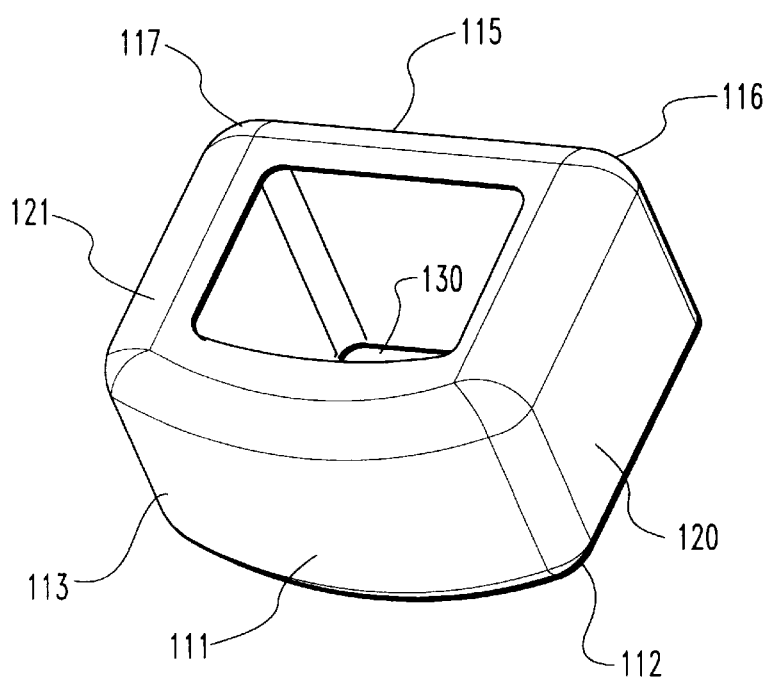
FIG. 2 is a front perspective view of the spacer of FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated spacers, and such further applications of the principles of the invention as illustrated therein being contemplated as would normally occur to one skilled in the art to which the invention relates.

The present invention provides spacers for engagement between vertebrae which are sized and configured to fill the space left after discectomy. The inventive spacers restore the height of the intervertebral disk space and provide immediate load bearing capability and support for the vertebral column without internal fixation. This invention eliminates the need for invasive autograft harvesting and trial and error trimming of graft material to fit the intra-distal space. The implants advantageously have an anatomically friendly shape and features which increase stability and decrease the risk of complications. In preferred embodiments, the spacers have the compressive strength of cortical bone with the advantage of incorporation of the spacer material without stress shielding. The migration resistance means prevents slippage, expulsion or micromotion. In this way, the spacers of this invention stimulate bone ingrowth like a bone graft and provide sufficient strength to support the vertebral column but avoid the disadvantages of both bone graft and metal implants such as graft migration, stress shielding and the presence of a permanent foreign body.

The migration resistance means increase post-operative stability of the spacer by engaging the adjacent vertebral endplates and anchoring the spacer to prevent expulsion. Such surface features also stabilize the bone-spacer interface and reduce micromotion to facilitate incorporation and fusion. These features also provide increased surface area which facilitates the process of bone healing and creeping substitution for replacement of the donor bone material and fusion.

In a specific embodiment, spacers are provided for engagement between vertebrae as depicted in FIGS. 1–4. Spacers of this invention can be conveniently incorporated into current surgical procedures such as, the Smith-Robinson technique for cervical fusion (Smith, M.D., G. W. and R. A. Robinson, M.D., "The Treatment of Certain Cervical-Spine Disorders By Anterior Removal Of The Intervertebral Disc And Interbody Fusion", *J. Bone And Joint Surgery,* 40-A:607–624 (1958) and Cloward, M.D., R. B., "The Anterior Approach For Removal Of Ruptured Cervical Disks", in meeting of the Harvey Cushing Society, Washington, D.C., Apr. 22, 1958). In such procedures, the surgeon prepares the endplates of the adjacent vertebral bodies to accept a graft after the disc has been removed. The endplates are generally prepared to be parallel surfaces with a high speed burr. The surgeon then typically sculpts the graft to fit tightly between the bone surfaces so that the graft is held by compression between the vertebral bodies. The bone graft is intended to provide structural support and promote bone ingrowth to achieve a solid fusion of the affected joint. The spacers of this invention avoid the need for this graft sculpting as spacers of known size and dimensions are provided. This invention also avoids the need for a donor surgery because the osteoinductive properties of autograft are not required. The spacers can be combined with osteoinductive materials that make allograft osteoinductive. Therefore, the spacers of this invention speed the patient's recovery by reducing surgical time, avoiding a painful donor surgery and inducing quicker fusion.

Figure 3:
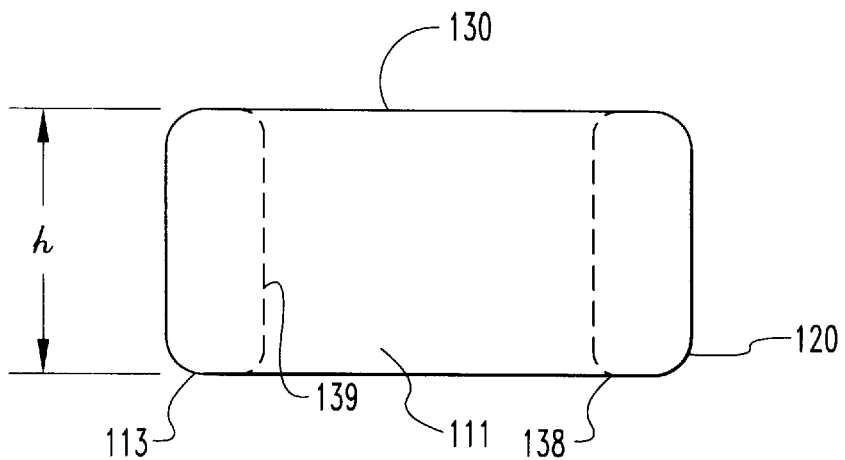
FIG. 3 is a front elevational view of the spacer depicted in FIG. 1.

The spacer 110 includes an anterior wall 111 having opposite ends 112, 113, a posterior wall 115 having opposite ends 116, 117 and two lateral walls 120, 121. Each of the lateral walls 120, 121 is connected between the opposite ends 112, 113, 116, 117 of the anterior 111 and posterior 115 walls to define a chamber 130. The walls are each composed of a bone composition, preferably cortical bone. The walls also include the superior face 135 which defines a first opening 136 in communication with the chamber 130. The superior face 135 includes a first, superior friction or vertebral engaging surface 137. As shown in FIG. 3, the walls further include an opposite inferior face 138 defining a second opening 139 which is in communication with the chamber 130. The chamber 130 is preferably sized to receive an osteogenic composition to facilitate bone growth. The inferior face 138 includes a second, inferior friction or second vertebral engaging surface (not shown) which is similar to or identical to the first friction or vertebral engaging surface 137.

The spacers of the present invention are preferably combined with an osteogenic material, such as a bone morphogenic protein (BMP). This combination provides structural support and enhances bone growth into and incorporation of the graft, resulting in fusion quicker than with graft alone.

Figure 4:
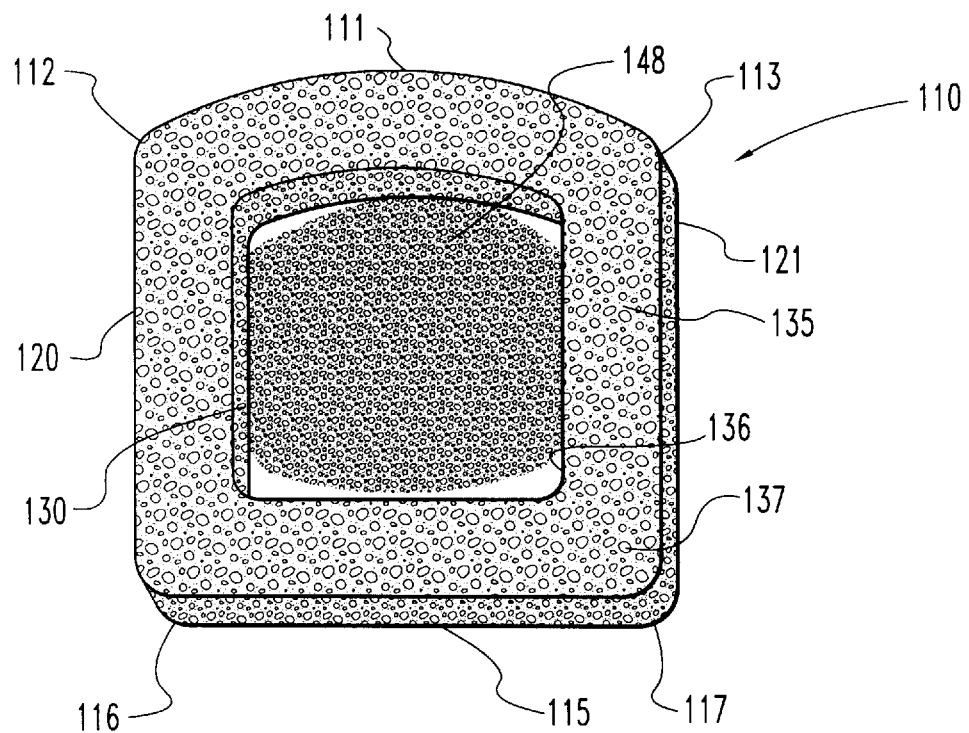
FIG. 4 is a top perspective view of the spacer of FIG. 1 showing the chamber packed with a collagen sponge.

An osteogenic material can be applied to the spacers of this invention by packing the chamber 130 with an osteogenic material 148 as shown in FIG. 4, by impregnating the graft with a solution including an osteogenic composition or by both methods combined. The composition may be applied by the surgeon during surgery or the spacer may be supplied with the composition preapplied. In such cases, the osteogenic composition may be stabilized for transport and storage such as by freeze-drying. The stabilized composition can be rehydrated and/or reactivated with a sterile fluid such as saline or water or with body fluids applied before or after implantation. Any suitable osteogenic material or composition is contemplated, including autograft, allograft, xenograft, demineralized bone, synthetic and natural bone graft substitutes, such as bioceramics and polymers, and osteoinductive factors. The term osteogenic composition used here means virtually any material that promotes bone growth or healing including natural, synthetic and recombinant proteins, hormones and the like.

Autograft can be harvested from locations such as the iliac crest using drills, gouges, curettes and trephines and other tools and methods which are well known to surgeons in this field. Preferably, autograft is harvested from the iliac crest with a minimally invasive donor surgery. The graft may include osteocytes or other bone reamed away by the surgeon while preparing the end plates for the spacer.

Advantageously, where autograft is chosen as the osteogenic material, only a very small amount of bone material is needed to pack the chamber 130. The autograft itself is not required to provide structural support as this is provided by the spacer 110. The donor surgery for such a small amount of bone is less invasive and better tolerated by the patient. There is usually little need for muscle dissection in obtaining such small amounts of bone. The present invention therefore eliminates many of the disadvantages of autograft.

The osteogenic compositions used in this invention preferably comprise a therapeutically effective amount of a substantially pure bone inductive factor to stimulate osteoinduction such as a bone morphogenetic protein in a pharmaceutically acceptable carrier. The preferred osteoinductive factors are the recombinant human bone morphogenic proteins (rhBMPs) because they are available in unlimited supply and do not transmit infectious diseases. Most preferably, the bone morphogenetic protein is a rhBMP-2, rhBMP-4 or heterodimers thereof. The concentration of rhBMP-2 is generally between about 0.4 mg/ml to about 1.5 mg/ml, preferably near 1.5 mg/ml. However, any bone morphogenetic protein is contemplated including bone morphogenetic proteins designated as BMP-1 through BMP-13. BMPs are available from Genetics Institute, Inc., Cambridge, Mass. and may also be prepared by one skilled in the art as described in U.S. Pat. Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenic protein from bone are described in U.S. Pat. No. 4,294,753 to Urist and Urist et al., 81 PNAS 371, 1984.

The choice of carrier material for the osteogenic composition is based on biocompatibility, biodegradability, mechanical properties and interface properties as well as the structure of the load bearing member. The particular application of the compositions of the invention will define the appropriate formulation. Potential carriers include calcium sulphates, polylactic acids, polyanhydrides, collagen, calcium phosphates, polymeric acrylic esters and demineralized bone. The carrier may be any suitable carrier capable of delivering the proteins. Most preferably, the carrier is capable of being eventually resorbed into the body. One preferred carrier is an absorbable collagen sponge marketed by Integra LifeSciences Corporation under the trade name Helistat® Absorbable Collagen Hemostatic Agent. Another preferred carrier is an open cell polylactic acid polymer (OPLA). Other potential matrices for the compositions may be biodegradable and chemically defined calcium sulfates, calcium phosphates such as tricalcium phosphate (TCP) and hydroxyapatite (HA) and including injectable bicalcium phosphates (BCP), and polyanhydrides. Other potential materials are biodegradable and biologically derived, such as bone or dermal collagen. Further matrices are comprised of pure proteins or extracellular matrix components. The osteoinductive material may also be an admixture of BMP and a polymeric acrylic ester carrier, such as polymethylmethacrylic.

For packing the chambers of the spacers of the present invention, the carriers are preferably provided as a sponge which can be compressed into the chamber or as strips or sheets which may be folded to conform to the chamber. Preferably, the carrier has a width and length which are each slightly greater than the width and length of the chamber. It may be preferable for the carrier to extend out of the openings of the chamber to facilitate contact of the osteogenic composition with the highly vascularized tissue surrounding the fusion site. When the carrier is provided in several strips sized to fit within the chamber, the strips can be placed one against another to fill the interior. As with the folded sheet, the strips can be arranged within the spacer in several orientations. Preferably, the osteogenic material, whether provided in a sponge, a single folded sheet or in several overlapping strips, has a length corresponding to the length and width of the chamber.

One preferred carrier is a biphasic calcium phosphate ceramic. Hydroxyapatite/tricalcium phosphate ceramics are preferred because of their desirable bioactive properties and degradation rates in vivo. The preferred ratio of hydroxyapatite to tricalcium phosphate is between about 0:100 and about 65:35. Any size or shape ceramic carrier which will fit into the chambers defined in the load bearing member are contemplated. Ceramic blocks are commercially available from Sofamor Danek Group, B. P. 4-62180 Rang-du-Fliers, France and Bioland, 132 Route d:Espagne, 31100 Toulouse, France. Of course, rectangular and other suitable shapes are contemplated. The osteoinductive factor is introduced into the carrier in any suitable manner. For example, the carrier may be soaked in a solution containing the factor.

In a preferred embodiment, an osteogenic composition is provided to the pores of the load bearing member. The bone growth inducing composition can be introduced into the pores in any suitable manner. For example, the composition may be injected into the pores of the graft. In other embodiments, the composition is dripped onto the graft or the graft is soaked in a solution containing an effective amount of the composition to stimulate osteoinduction. In either case the pores are exposed to the composition for a period of time sufficient to allow the liquid to throughly soak the graft. The osteogenic factor, preferably a BMP, may be provided in freeze-dried form and reconstituted in a pharmaceutically acceptable liquid or gel carrier such as sterile water, physiological saline or any other suitable carrier. The carrier may be any suitable medium capable of delivering the proteins to the spacer. Preferably the medium is supplemented with a buffer solution as is known in the art. In one specific embodiment of the invention, rhBMP-2 is suspended or admixed in a carrier, such as water, saline, liquid collagen or injectable BCP. The BMP solution can be dripped into the graft or the graft can be immersed in a suitable quantity of the liquid. In a most preferred embodiment, BMP is applied to the pores of the graft and then lypholized or freeze-dried. The graft-BMP composition can then be frozen for storage and transport.

Figure 5:
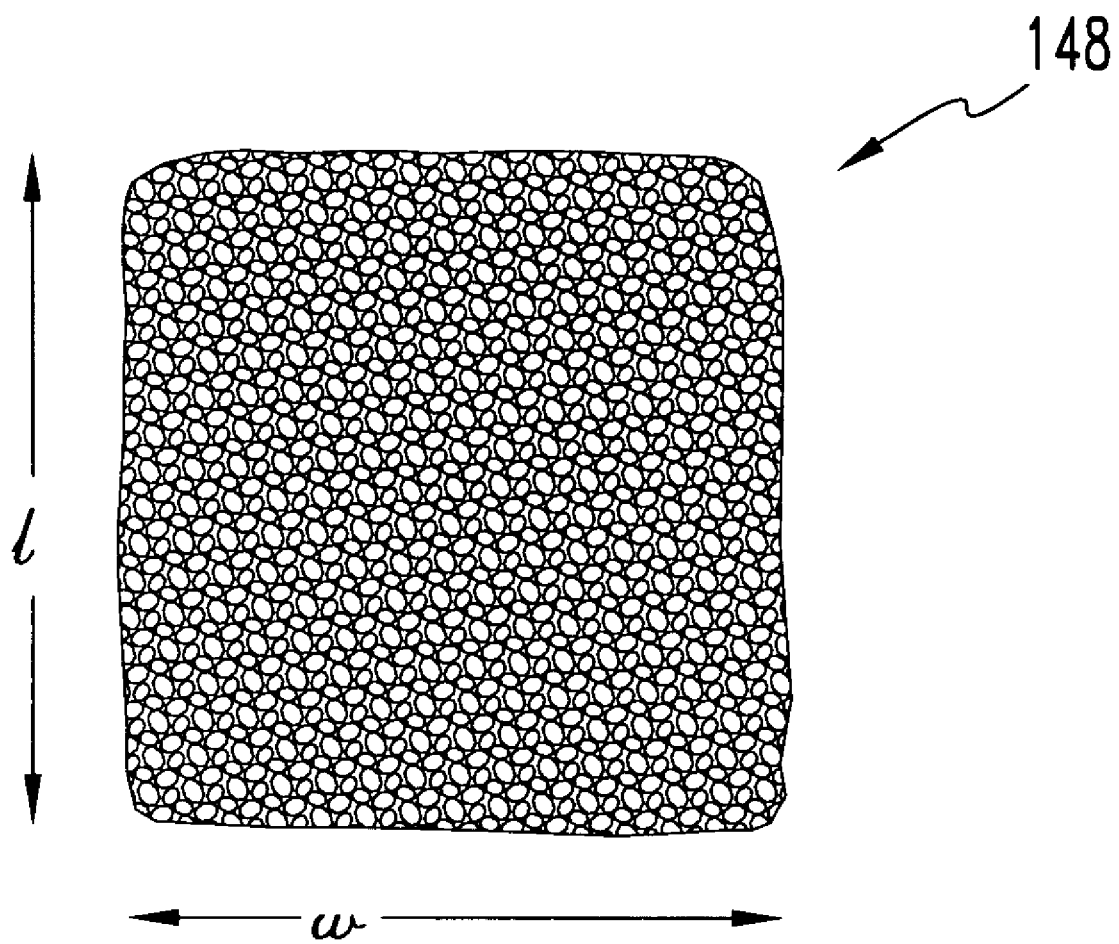
FIG. 5 is a top elevational view of a collagen sponge.

In one specific embodiment shown in FIGS. 4 and 5, the D-shaped spacer 110 includes a collagen sponge 148 having a width w and length l which are each slightly greater than the width W and length L of the chamber. In a preferred embodiment, the sponge 148 is soaked with freeze dried rhBMP-2 reconstituted in buffered physiological saline and then compressed into the chamber 130. The sponge 148 is held within the chamber 130 by the compressive forces provided by the sponge 148 against the walls 111, 115, 120, 121 of the spacer 110.

The spacers may be of any suitable shape, such as oval, rectangular and kidney-shaped. However, in one specific embodiment, the spacer is D-shaped. The anterior wall 111 as shown in FIGS. 1–4 has a convexly curved anterior surface 114. This anterior curvature is preferred to conform to the geometry of the adjacent vertebral bone and specifically to the harder cortical bone of the vertebrae. The D-shape of the spacer 110 also prevents projection of the anterior wall 111 outside the anterior aspect of the disc space, which can be particularly important for spacers implanted in the cervical spine.

The spacers are shaped advantageously for cervical arthrodesis. The flat posterior and lateral walls 115, 120 and 121, as shown in FIG. 1, can be easily incorporated into a Smith Robinson surgical fusion technique. After partial or total discectomy and distraction of the vertebral space, the surgeon prepares the end plates for the spacer 110 preferably to create flat posterior and lateral edges. The spacer 110 fits snugly with its flat surfaces against the posterior and lateral edges which prevents medial and lateral motion of the spacer 110 into vertebral arteries and nerves. This also advantageously reduces the time required for the surgery by eliminating the trial and error approach to achieving a good fit with bone grafts because the spacers can be provided in predetermined sizes.

Figure 6:
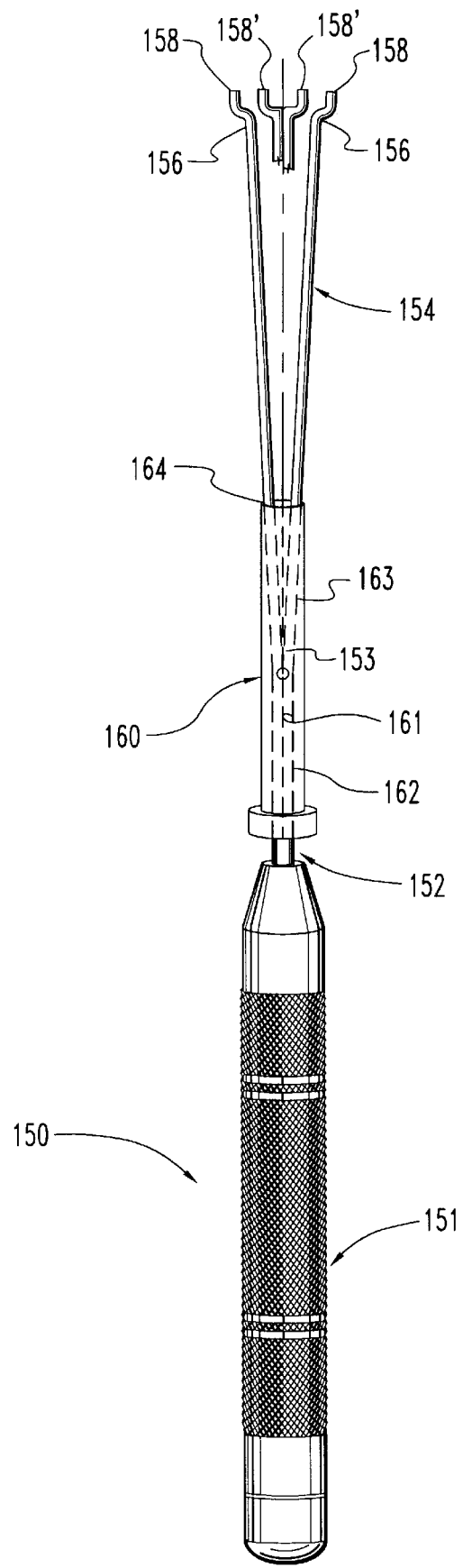
FIG. 6 is an implant insertion device.

Devices such as the spacer 110 can be inserted into the fusion site during an open or percutaneous surgery using an insertion device such as the one depicted in FIG. 6. The inserter 150 includes a handle 151 with knurlings or other suitable patterns to enhance manual gripping of the handle. A shaft 152 extends from the handle 151 and is generally divided into two portions: a solid portion 153 and a split jaw portion 154. The split jaw portion 154 is at the distal end of the shaft 152 opposite the handle 151. In the preferred embodiment, the split jaw portion 154 includes two jaws 156 each having an offset gripping surface 158 at their free ends. As depicted in FIG. 6 the split jaw portions 154 are movable from a fully opened position as represented by the fully separated position of the gripping surfaces 158. The split jaw portion 154 is closeable to a fully closed position in which the two jaws 156 are in contact with one another. In the fully closed position, the gripping surfaces, identified as 158' in FIG. 6, are separated by a distance sufficiently close to grip a hollow spacer 110 therebetween. In particular, the closed gripping surfaces 158' contact the side surfaces of the two lateral walls 120, 121 of the spacer 110. In one preferred embodiment, the gripping surfaces 158 are roughened or knurled to enhance the grip on the spacer 110.

The inserter 150 further includes a sleeve 160 that is concentrically disposed around shaft 152. Preferably the sleeve 160 defines an inner bore 161 with a first portion 162 having a diameter slightly greater than the diameter of shaft 152. The internal bore 161 includes a flared portion 163 at its distal end 164. In the preferred embodiment, when the jaws 156 of the split jaw portion 154 are in their fully opened position, the jaws contact the flared portion 63 of the bore 161.

In the use of the inserter 150, the sleeve 160 is slid along the shaft 152, and more particularly along the opened jaws 156, to push the jaws together. As the jaws are pushed together, the gripping surfaces 158 engage and firmly grip a spacer 110 as described above. This inserter can then be extended percutaneously into the surgical site to implant a spacer 110 in the intra-discal space. Once the spacer is properly positioned, the sleeve 160 can be moved back toward the handle 151, so that the natural resilience of the two jaws 156 cause them to spread apart, thereby releasing the spacer 110. The inserter 150 can then be withdrawn from the surgical site with the jaws fully opened, or the sleeve can be advanced along the shaft once the gripping surfaces 158 have cleared the spacer 110. Other details of a similar device are disclosed in commonly assigned, pending U.S. application Ser. No. 08/697,784, IMPLANT INSERTION DEVICE. Metal spacers, insertion devices and methods relating to the same are disclosed in commonly assigned and co-pending applications: U.S. patent application Ser. No. 08/603,675, VERTEBRAL SPACER, U.S. patent application Ser. No. 08/603,676, INTERVERTEBRAL SPACER and U.S. patent application, Attorney Docket No. 97:59:PA/4002-1612.

Figure 7:
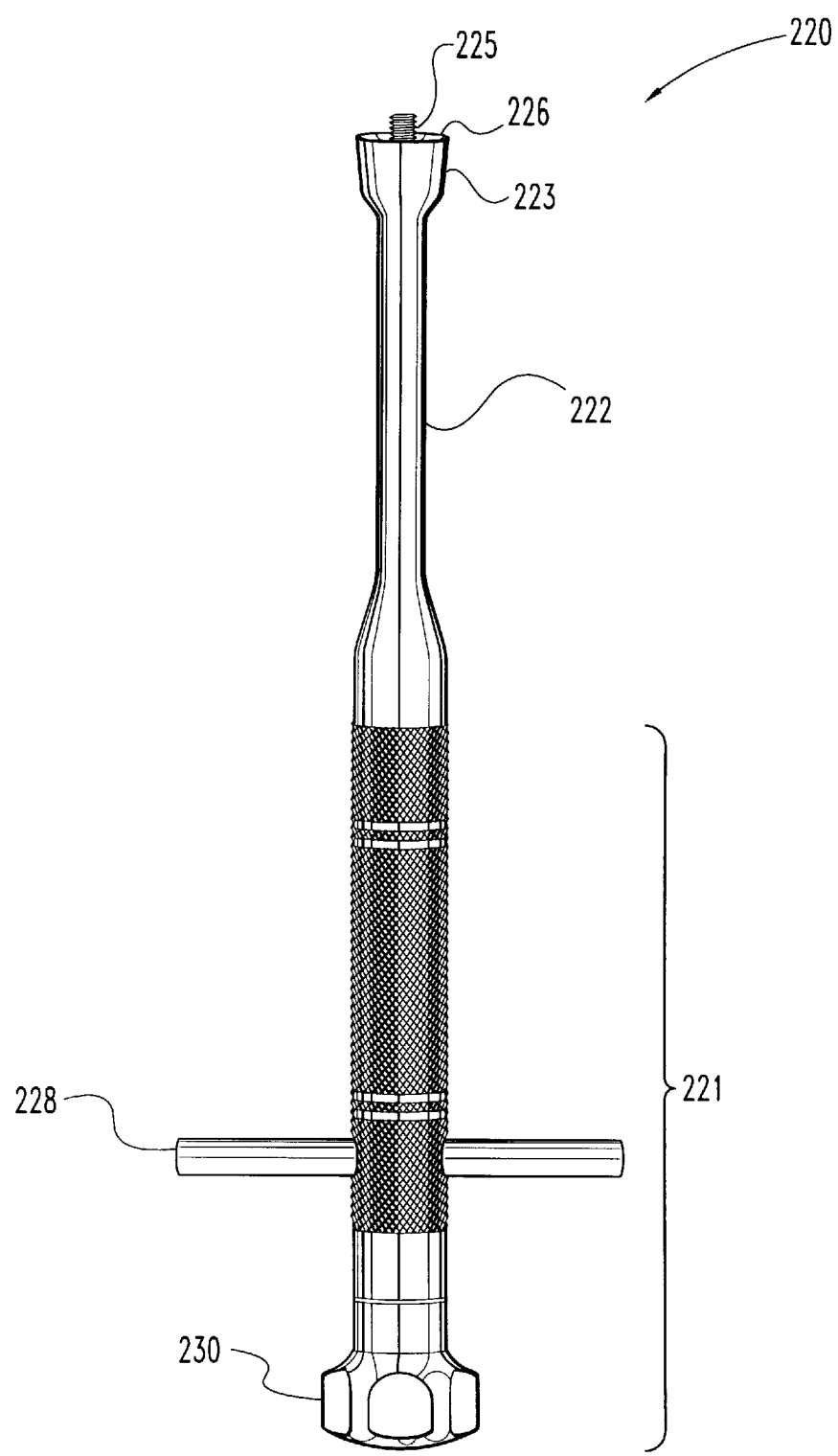
FIG. 7 depicts a side elevational view of an implanting tool.
Figure 8:
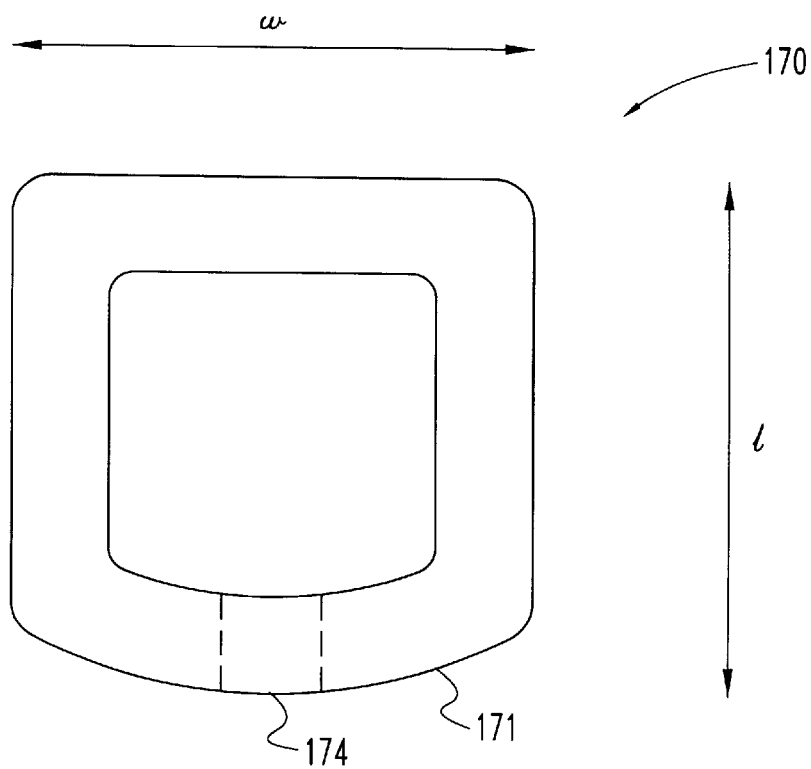
FIG. 8 is a D-spaced spacer of this invention having a tool engaging hole.
Figure 9:
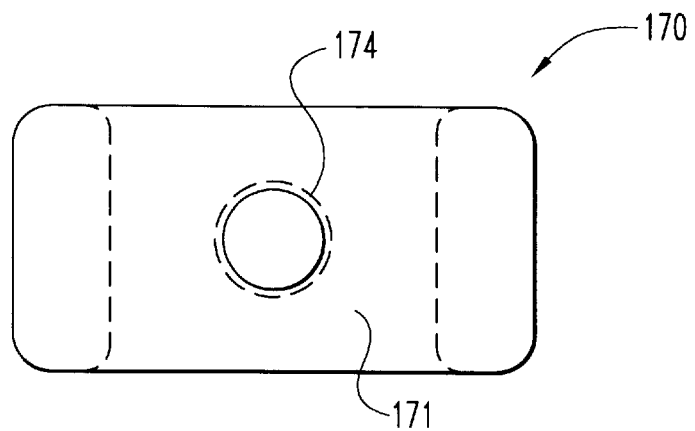
FIG. 9 is a front elevational view of the spacer FIG. 8.

Alternatively, the spacers of this invention may be provided with a tool engaging hole for insertion such as the tool depicted in FIG. 7. According to another specific embodiment depicted in FIGS. 8 and 9, the spacer 170 includes an anterior wall 171 defining a tool engaging hole 174. In a most preferred embodiment, the tool engaging hole 174 is threaded for receiving a threaded implanting tool such as depicted in FIG. 7. The inserter 220 includes a handle portion 221 with knurlings or other suitable patterns to enhance manual gripping of the handle. A shaft 222 extends from the handle 221. The distal end 223 of the shaft 222 includes a tip 225 which mates with the tool engaging hole 174. Preferably the tip 225 and tool engaging hole 174 have corresponding mating threads 226, 178. Where the tool engaging hole 174 is defined in a curved wall as shown in FIG. 8, the distal end 223 of the shaft 222 preferably includes a curved portion 224 that conforms to the curved anterior surface of the spacer. The inserter 220 also preferably includes a T-handle 228 for spacer control and positioning. Preferably the inserter 120 includes means for rotating the threaded tip 225. In FIG. 7, the knob 230 is engaged to the tip 225 via an inner shaft extending through an internal bore (not shown) in the handle 221 and shaft 222. The tip 225 is preferably at the end of the inner shaft with the inner shaft rotatingly mounted within the handle 221 and shaft 222.

In the use of the inserter 220, a spacer 170 is engaged to the threaded tip 225 with the curved portion 224 flush with the anterior wall 171. The inserter and spacer can then be extended percutaneously into the surgical site to implant the spacer in the intra-discal space. Once the spacer 170 is properly positioned, the knob 230 can be turned to rotate the threaded tip 225 and disengage the tip from the hole 174 of the spacer 110. The inserter 220 can then be withdrawn from the surgical site leaving the spacer 170 in place.

Figure 10:
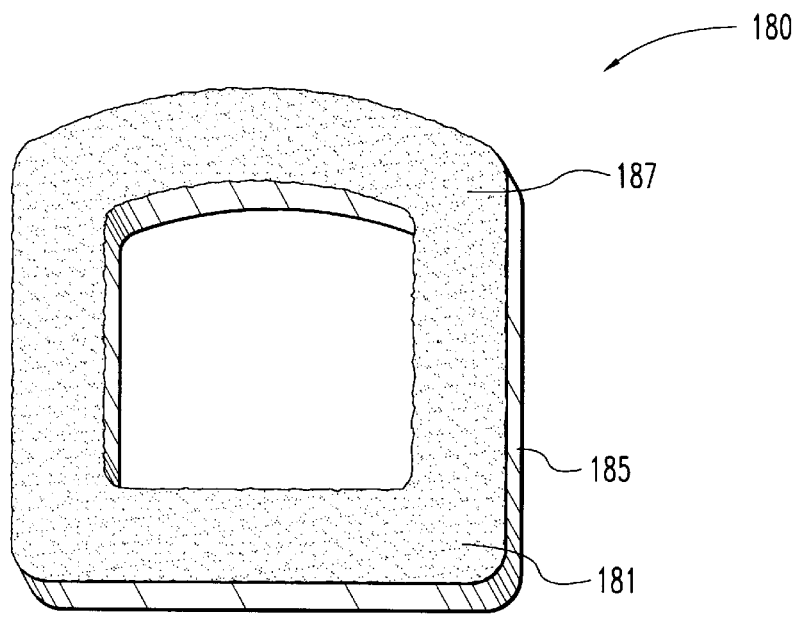
FIG. 10 is top elevational view of another embodiment of the spacer.
Figure 11:
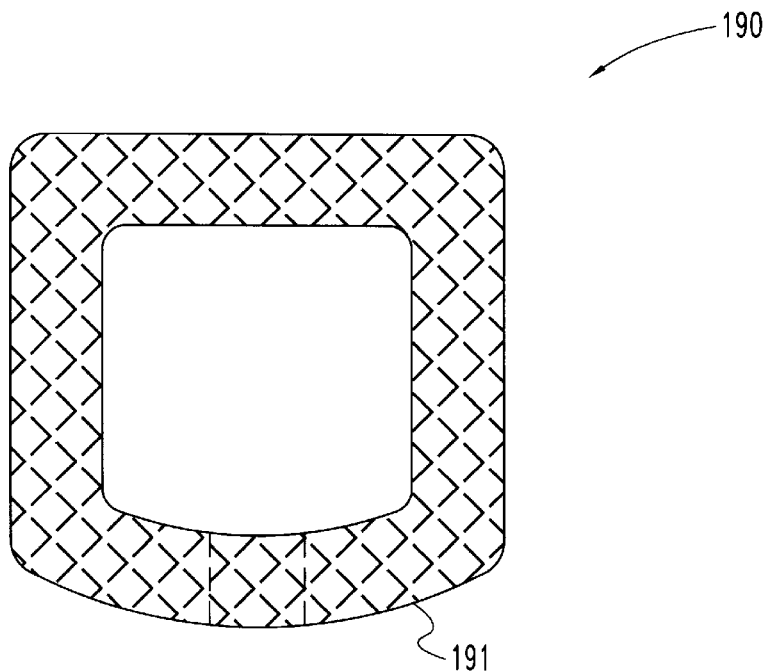
FIG. 11 is a top elevational view of another embodiment of the spacer.
Figure 12:
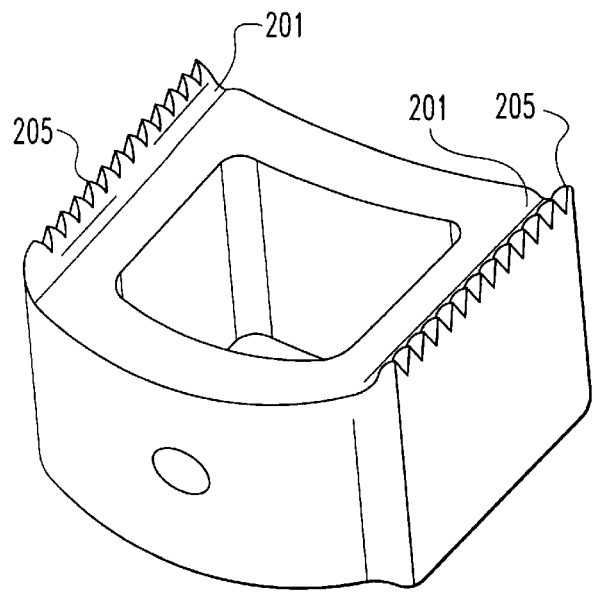
FIG. 12 is a top perspective view of another embodiment of the spacers of this invention having teeth.
Figure 13:
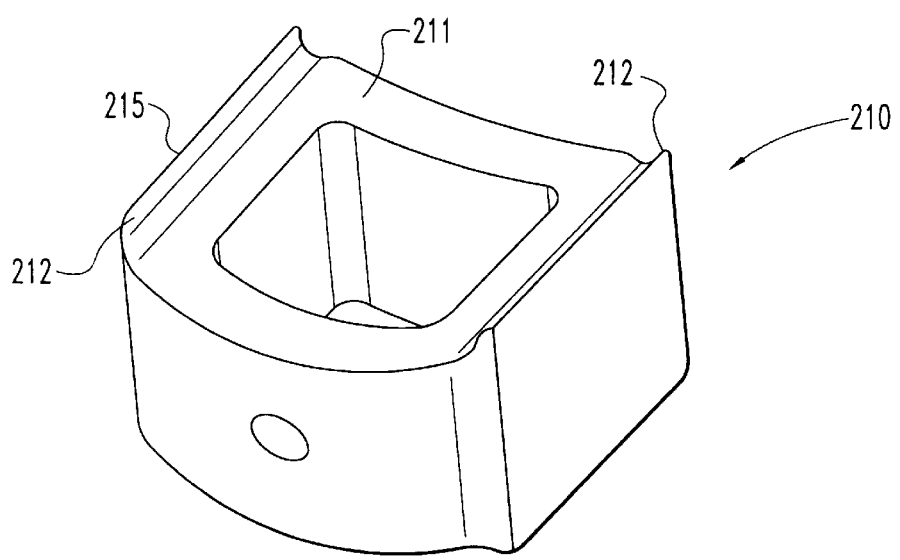
FIG. 13 is a top elevational view of another embodiment of the spacer having blades.
Figure 14:
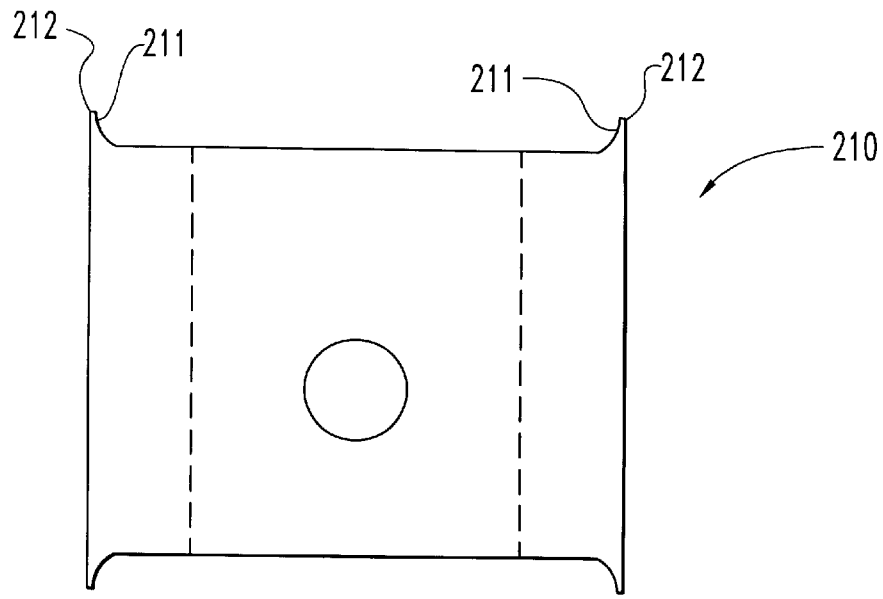
FIG. 14 is a front elevational view of the spacer of FIG. 13.

In preferred embodiments, the spacers are provided with migration resistance means. The engaging surfaces of the spacers can be machined to facilitate engagement with the endplates of the vertebrae and prevent slippage of the spacer as is sometimes seen with smooth grafts prepared at the time of surgery. Referring now to FIG. 10, the spacer 180 may be provided with a roughened surface 181 on one of the engaging surfaces 187 of one or both of the superior face 185 or inferior face (not shown). The roughened surface 191 of the spacer 190 may include a waffle or other suitable pattern as depicted in FIG. 11. In one preferred embodiment shown in FIG. 12, the engaging surfaces 201 include teeth 205 which provide biting engagement with the endplates of the vertebrae. In another embodiment (FIGS. 13 and 14), the spacer 210 includes engaging surfaces 211 machined to include one or more blades 212. Each blade includes a cutting edge 213 configured to pierce a vertebral end-plate. The blade 212 can be driven into the bone surface to increase the initial stability of the spacer.

In a preferred embodiment depicted in FIGS. 15–18, the migration resistance means includes a set of expulsion resistance grooves defined in the body 301 of the spacer 300. In this spacer, the superior and inferior vertebral engaging surfaces 337 and 340 define a set of migration resistance grooves 350. As shown more clearly in FIG. 18 each of the grooves 350 includes a first face 355. The first face 355 defines an angle $\alpha_1$ no more than about 90° relative to the engaging surface 337. Preferably, the angle $\alpha_1$ is 90°. In other words, the first face 355 is preferably perpendicular to the engaging surface 337. Each groove 350 also includes a second, opposing and sloped face 360. The sloped face 360 preferably forms an angle $\alpha_2$ relative to a line 1 which is parallel to the first face 355. The first face 355 and second face 360 define a pocket 370 therebetween for trapping vertebral bone.

Preferably each of the grooves 350 of the set 302 are arranged in series in that each second face 360 slants in the same direction as the others. In the embodiment shown in FIGS. 15–18, each of the grooves 350 slants away from the posterior or second end 315 and towards the first end or anterior wall 311 of the body 301. In this embodiment the engaging surface 337 defines a peak 375 between each of the grooves 350. The peak 375 preferably defines a flattened surface. The vertebral engaging surface 337 may be provided with a cutting edge 380 between the first face 355 and the engaging surface 375.

Figure 19:
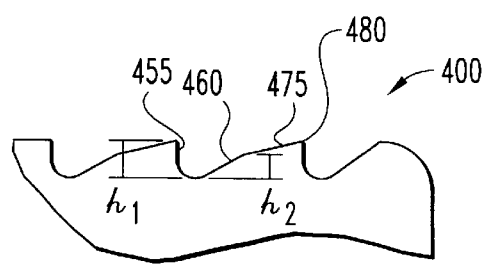
FIG. 19 is a side elevational detailed view of the surface of another spacer of this invention.

Referring now to the spacer 400 of FIG. 19, the exact configuration of the grooves may vary. For example, the first face 355 may have a first height $h_1$ between the pocket 470 and the engaging surface 437 which is taller than a second height $h_2$ of the second face 460. In this embodiment, the peak 475 is sloped toward the cutting edge 480.

In preferred embodiments, the pocket 370 is substantially arcuate or circular in shape. The pocket is configured for collecting and trapping vertebral bone if the spacer migrates after it is implanted. For example, the embodiment depicted in FIGS. 15–18 has grooves that resist migration in the direction of the arrow A. If the spacer is implanted with the first or anterior end 311 to the anterior of the patient using an anterior approach, the anterior tissues will be weakened and migration will most likely occur in the anatomically anterior direction. The spacer can be configured for implantation with the grooves facing in a direction that resists that anterior migration. If a force urges the spacer 300 in the anterior direction, the edge 380 of the peak 375 will dig into the vertebral bone and bone will collect in the pocket 370.

Figure 20:
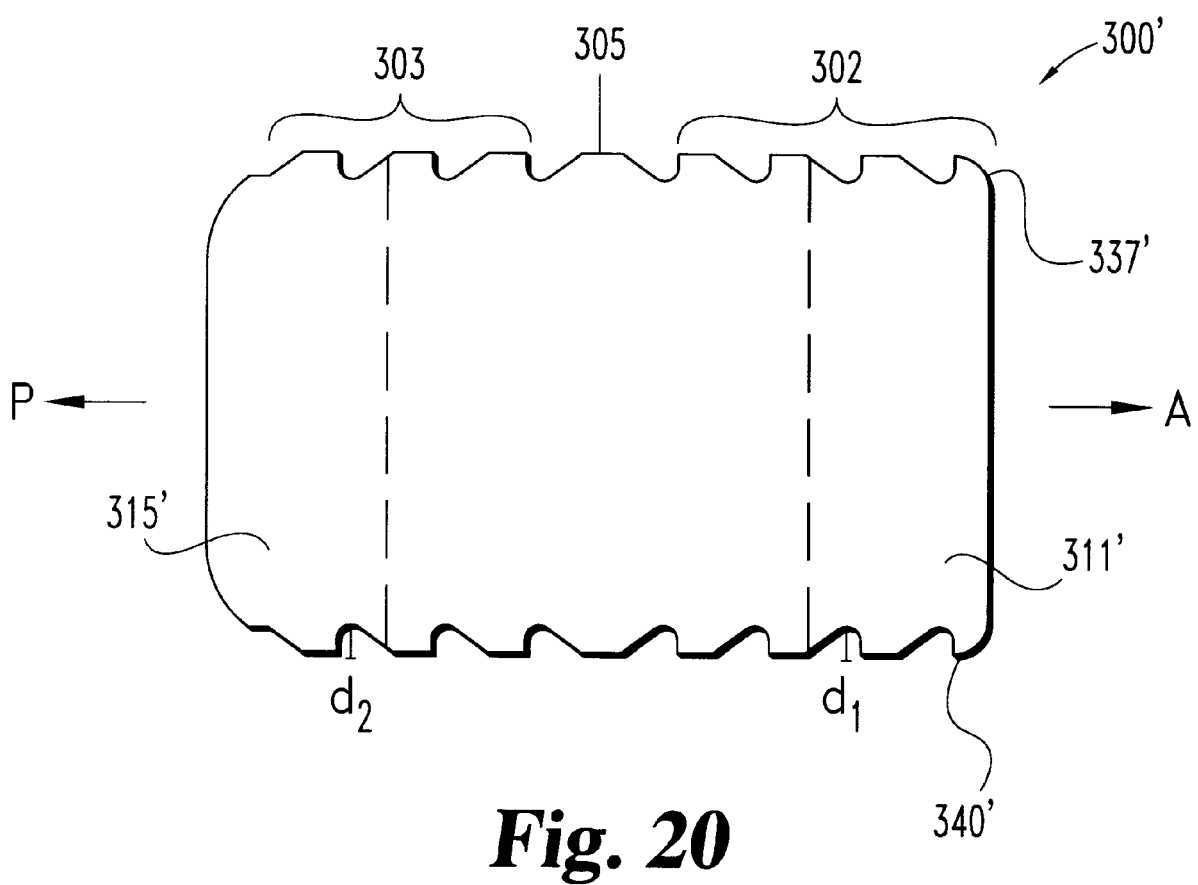
FIG. 20 is a top elevational view of another embodiment of the spacer having two sets of migration resistance grooves.

The spacers of this invention may also be provided with means that resist migration in two directions. Referring now to FIG. 20, the spacer 300' includes a first set of grooves 301 which resist migration in the direction of arrow A and a second set of grooves 302 which resist migration in the direction of arrow P. The two sets of grooves 302 and 303 meet at a flattened bridge member 305. The first set of grooves 302 slants towards the first end 311' and resists migration in the direction of the arrow A. The second set of grooves 303 slants towards the second end 315' and resist migration in the direction of the arrow P. In this way the grooves resist micromotion, migration and expulsion.

As shown in FIG. 20, the depth of the grooves may vary between the two sets 302 and 303. The grooves of the two sets 302 and 303 have a depth $d_1$, $d_2$ below the vertebral engaging surface 337' and 340'. The grooves of the first set 302 or the second set 303 may be deeper than the other as needed for the particular application.

The spacers of this invention are preferably formed of a bone composition or material. The bone may be autograft, allograft, xenograft or any of the above prepared in a variety of ways. Cortical bone is preferred for its compressive strength. In one embodiment, the spacers are obtained as a cross sectional slice of a shaft of a long bone. For example, various shaped spacers may be obtained by machining a cortical ring into the desired configuration. The exterior surfaces of the walls can be formed by machining the ring to a D-shape. Material from the medullary canal of the ring can be removed to form a chamber. Surface features and migration resistance means can be defined into the surface of the spacers using conventional machining methods and a standard milling machine which have been adapted to bone. Various methods and procedures are known for treating and processing bone to provide bone materials and compositions. These methods and procedures can be applied to the present invention as long as the resulting bone material provides a sufficient compressive strength for the intended application.

Figure 15:
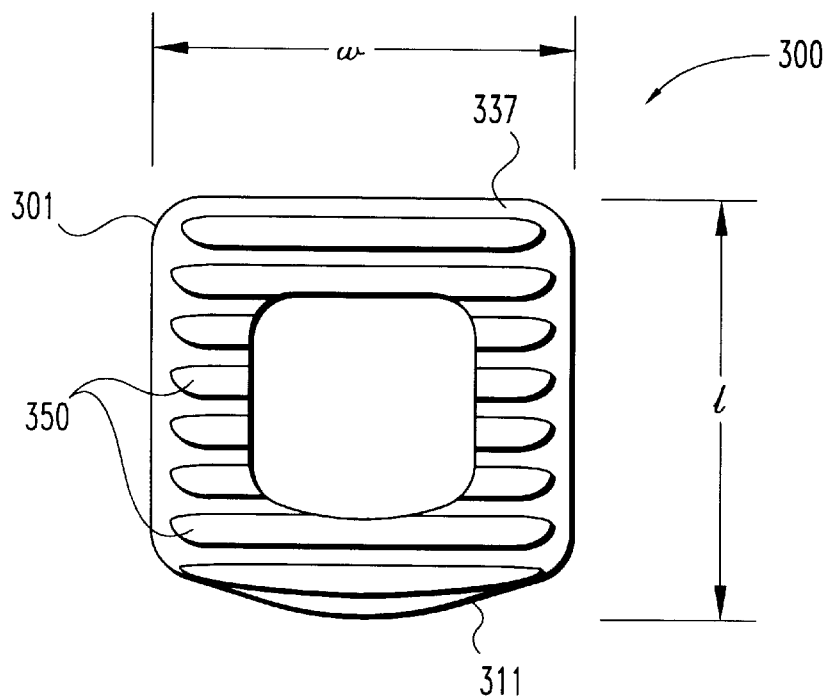
FIG. 15 is a top elevational view of a spacer having migration resistance grooves.
Figure 16:
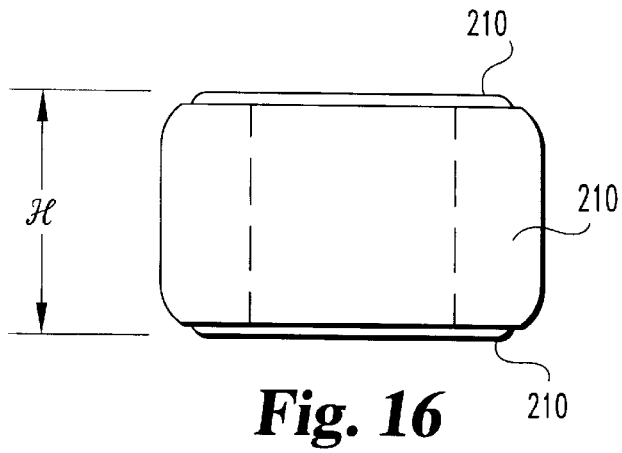
FIG. 16 is a front elevational view of the spacer of FIG. 15.
Figure 17:
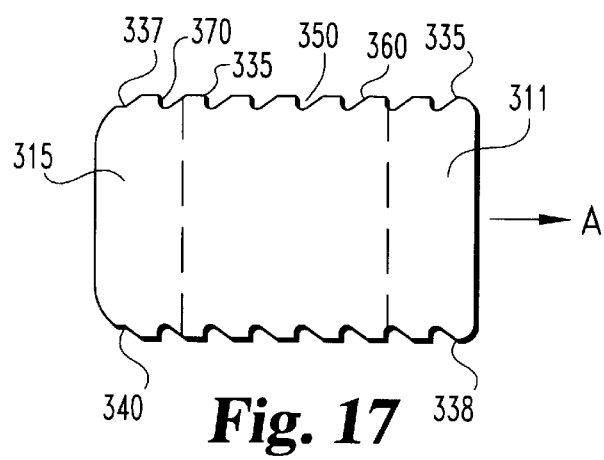
FIG. 17 is a side elevational view of the spacer of FIG. 15.
Figure 18:
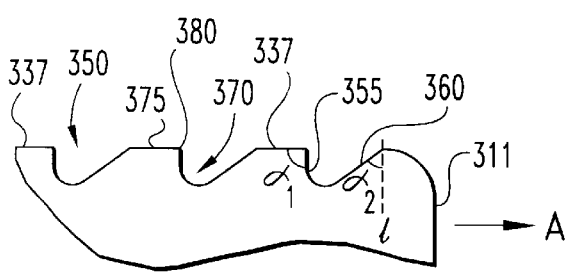
FIG. 18 is a side elevational detailed view of the surface of the spacer of FIG. 15.

Spacers of the present invention can be made to any suitable size or shape which is suitable for the intended application. Referring now to FIGS. 15 and 16, the spacer has a width W of preferably 11 to 14 millimeters, a length L of preferably between about 11 and 14 millimeters and a height H of about 7 millimeters. The height H is the distance between the highest peak 375 on the superior vertebral engaging surface 337 and the highest peak 375 on the inferior vertebral engaging surface 340.

Advantageously, the intervertebral spacers of the present invention may not require internal fixation. The spacers are contained by the compressive forces of the surrounding ligaments and muscles, and the disc annulus if it has not been completely removed. Temporary external immobilization and support of the instrumented and adjacent vertebral levels, with a cervical collar, lumbar brace or the like, is generally recommended until adequate fusion is achieved.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed:

1. A spinal spacer for engagement between vertebrae, comprising:
    a body formed of a bone composition and including a first end, an opposite second end, a superior face defining a superior vertebral engaging surface and an inferior face defining an inferior vertebral engaging surface; and
    at least one of said vertebral engaging surfaces defining a first set of migration resistance grooves, each of said grooves including a first face defining an angle of no more than about 90 degrees relative to said one of said engaging surfaces and a second opposing sloped face, said first and second faces defining a substantially arcuate pocket therebetween for trapping vertebral bone.

2. The spacer of claim 1 wherein said grooves of said first set are arranged in series.

3. The spacer of claim 2 wherein each of said sloped faces is sloped toward said first end.

4. The spacer of claim 1 wherein said at least one of said vertebral engaging surfaces defines a peak between each of said grooves, said peak defining a flattened surface.

5. The spacer of claim 3 further comprising a second set of migration resistance grooves defined in series in at least one of said vertebral engaging surfaces, each of said grooves of said second set including a first face defining an angle of no more than about 90 degrees relative to said one of said engaging surfaces and a second opposing sloped face, said first and second faces of each of said grooves of said second set defining a pocket therebetween for trapping vertebral bone, each of said sloped faces of said second set sloping towards said second end.

6. The spacer of claim 5 wherein each of said grooves has a depth below said at least one of said vertebral engaging surfaces and said grooves of said first set are deeper than said grooves of said second set.

7. The spacer of claim 5 wherein each of said grooves has a depth below said at least one of said vertebral engaging surfaces and said grooves of said second set are deeper than said grooves of said first set.

8. The spacer of claim 1 wherein the pocket defined by said first and second faces is circularly rounded.

9. The spacer of claim 1 wherein said first face is perpendicular to said at least one of said vertebral engaging surfaces.

10. The spacer of claim 1 further comprising a cutting edge between said first face and said at least one of said vertebral engaging surfaces.

11. The spacer of claim 4 wherein said first face at said pocket has a first height which is taller than a second height of said second face at said pocket, and said peak is sloped.

12. The spacer of claim 1 wherein said superior face defines a first opening and said inferior face defines a second opening, each of said openings in communication with a chamber formed through said body.

13. The spacer of claim 12 wherein said first end defines a convexly curved surface.

14. The spacer of claim 13 wherein said second end is flat.

15. A hollow spinal spacer for engagement between vertebrae, comprising:

a body formed of bone composition and including an anterior wall with opposite ends and defining a convexly curved anterior surface, an opposite posterior wall having opposite ends and defining a flat posterior surface, two lateral walls, each integrally connected between said opposite ends of said anterior and posterior walls to define a chamber, said walls further defining a superior vertebral engaging surface defining a first opening, said first opening in communication with said chamber, and an inferior vertebral engaging surface defining a second opening, said second opening in communication with said chamber; and at least one of said vertebral engaging faces defining a set of migration resistance grooves, each of said grooves including a first face defining an angle of no more than about 90 degrees relative to said one of said engaging surfaces and a second opposing sloped face, said first and second faces defining a substantially arcuate pocket therebetween for trapping vertebral bone, said grooves in series with said sloped faces sloping towards said anterior wall.

16. A spinal spacer for engagement between vertebrae, comprising:

a body formed of a bone composition and including a first end, an opposite second end, a superior face defining a superior vertebral engaging surface and an inferior face defining an inferior vertebral engaging surface; and at least one of said vertebral engaging surfaces defining a first set of migration resistance grooves, each of said grooves including a first face defining an angle of no more than about 90 degrees relative to said one of said engaging surfaces and a second opposing sloped face, said first and second faces defining a pocket therebetween for trapping vertebral bone, said one of said engaging surfaces defining a peak between each of said grooves, said peak defining a flattened surface.

17. The spacer of claim 16 further comprising a cutting edge between said first face and said at least one of said vertebral engaging surfaces.

18. The spacer of claim 16 wherein said first face at said pocket has a first height which is taller than a second height of said second face at said pocket, and said peak is sloped.

19. The spacer of claim 16 wherein said first face is perpendicular to said at least one of said vertebral engaging surfaces.

20. A spinal spacer for engagement between vertebrae, comprising:

a body formed of a bone composition and including a first end, an opposite second end, a superior face defining a superior vertebral engaging surface and an inferior face defining an inferior vertebral engaging surface; and at least one of said vertebral engaging surfaces defining a first set of migration resistance grooves, said at least one of said vertebral engaging surfaces defining a second set of migration resistance grooves, each of said grooves including a first face defining an angle of no more than about 90 degrees relative to said one of said engaging surfaces and a second opposing sloped face, said first and second faces defining a pocket therebetween for trapping vertebral bone, each of said sloped faces of said grooves of said first set sloping toward said first end, each of said sloped faces of said grooves of said second set sloping toward said second end.

21. The spacer of claim 20 wherein each of said grooves has a depth below said at least one of said vertebral engaging surfaces and said grooves of said first set are deeper than said grooves of said second set.

22. The spacer of claim 20 wherein each of said grooves has a depth below said at least one of said vertebral engaging surfaces and said grooves of said second set are deeper than said grooves of said first set.

23. The spacer of claim 20 wherein said at least one of said vertebral engaging surfaces defines a peak between each of said grooves, said peak defining a flattened surface.

24. The spacer of claim 23 wherein said first face at said pocket has a first height which is taller than a second height of said second face at said pocket, and said peak is sloped.

* * * * *

UNITED STATES PATENT AND TRADEMARK OFFICE
CERTIFICATE OF CORRECTION

PATENT NO : 5,989,289
DATED : November 23, 1999
INVENTOR(S) : Bradley J. Coates et al.

It is certified that error appears in the above-identified patent and that said Letters Patent is hereby corrected as shown below:

On the title page, item [63] the "Related U.S. Application Data" section, please delete the current text and replace it with the following:

-- Continuation of application No. 08/902,937, Jul. 30, 1997, abandoned, which is a continuation-in-part of application No. 08/740,031, Oct. 23, 1996; and of application No. 08/603,676, Feb. 20, 1996, abandoned, which is a continuation-in-part of application No. 08/543,563, Oct. 16, 1995, abandoned; and of application No. 08/603,675, Feb. 20, 1996, abandoned, which is a continuation-in-part of application No. 08/543,563, Oct. 16, 1995, abandoned. --

In col. 1, line 6, please delete ", which is a continuation-in-part application of" and insert in lieu thereof -- ; and of --.

In col. 1, line 9, please insert -- of -- in between "and" and "Ser.".

Signed and Sealed this

Twenty-seventh Day of March, 2001

*Attest:*

NICHOLAS P. GODICI

*Attesting Officer*   *Acting Director of the United States Patent and Trademark Office*

UNITED STATES PATENT AND TRADEMARK OFFICE
CERTIFICATE OF CORRECTION

| | |
|---|---|
| PATENT NO. | : 5,989,289 |
| APPLICATION NO. | : 08/948135 |
| DATED | : November 23, 1999 |
| INVENTOR(S) | : Bradley J. Coates et al. |

It is certified that error appears in the above-identified patent and that said Letters Patent is hereby corrected as shown below:

<u>Title Page, Item (63) delete the Related U.S. Application Data and insert the following text in lieu thereof:</u>

-- This application is a continuation of application No. 08/902,937, filed July 30, 1997, now abandoned, which is a continuation-in-part of: application No. 08/740,031, filed October 23, 1996, now abandoned, which is a continuation-in-part of application No. 08/603,676, filed February 20, 1996, now Pat. No. 6,423,095, which is a continuation-in-part of application No. 08/543,563, filed October 16, 1995, now abandoned; and of application Serial No. 08/603,676, filed February 20, 1996, now Pat. No. 6,423,095, which is a continuation-in-part of application No. 08/543,563, filed October 16, 1995, now abandoned; and of application No. 08/603,675, filed February 20, 1996, now abandoned, which is a continuation-in-part of application No. 08/543,563, filed October 16, 1995, now abandoned. --.

<u>Column 1, line 4:</u>
Change "of" to -- of: --.

<u>Column 1, line 5:</u>
Change "pending" to -- now abandoned --.

<u>Column 1, line 6:</u>
Change "abandoned" to -- U.S. Patent No. 6,423,095 --.

<u>Column 1, line 8:</u>
After "and" add -- of application No. 08/603,676, filed Feb. 20, 1996, now Pat. No. 6,423,095, which is a continuation-in-part of application No. 08/543,563, filed Oct. 16, 1995, now abandoned; and of --.

Signed and Sealed this
Fourteenth Day of February, 2012

David J. Kappos
*Director of the United States Patent and Trademark Office*